(12) United States Patent
Taylor

(10) Patent No.: US 9,171,443 B2
(45) Date of Patent: Oct. 27, 2015

(54) MARKING MATERIAL

(75) Inventor: Christopher Taylor, Tamworth (GB)

(73) Assignee: APPLIED DNA SCIENCES, INC., Stony Brook, NY (US)

( * ) Notice: Subject to any disclaimer, the term of this patent is extended or adjusted under 35 U.S.C. 154(b) by 906 days.

(21) Appl. No.: 12/307,488

(22) PCT Filed: Jul. 6, 2007

(86) PCT No.: PCT/GB2007/002545
§ 371 (c)(1),
(2), (4) Date: Oct. 26, 2009

(87) PCT Pub. No.: WO2008/007060
PCT Pub. Date: Jan. 17, 2008

(65) Prior Publication Data
US 2010/0065463 A1    Mar. 18, 2010

(30) Foreign Application Priority Data
Jul. 8, 2006  (GB) .................................. 0613626.1

(51) Int. Cl.
*C09K 3/30* (2006.01)
*C12Q 1/68* (2006.01)
*G08B 15/02* (2006.01)

(52) U.S. Cl.
CPC ...................................... *G08B 15/02* (2013.01)

(58) Field of Classification Search
CPC . C09K 3/30; Y10S 524/903; C12Q 2563/185
USPC ............ 516/14, 15, 18; 514/44; 524/47, 156, 524/903; 424/47; 536/24.3
See application file for complete search history.

(56) References Cited

U.S. PATENT DOCUMENTS

| | | | | | |
|---|---|---|---|---|---|
| 5,156,765 | A | * | 10/1992 | Smrt et al. | 516/14 |
| 5,429,952 | A | * | 7/1995 | Garner et al. | 436/518 |
| 5,763,176 | A | * | 6/1998 | Slater et al. | 435/6.11 |
| 2003/0035917 | A1 | * | 2/2003 | Hyman | 428/67 |

FOREIGN PATENT DOCUMENTS

| | | | |
|---|---|---|---|
| EP | 0774012 B1 | * | 12/1994 |
| GB | 2319337 A | | 5/1998 |
| WO | 99/45514 A1 | | 9/1999 |
| WO | 00/61799 A2 | | 10/2000 |
| WO | 02/066678 A2 | | 8/2002 |
| WO | 2004/086323 A1 | | 10/2004 |
| WO | 2008/007060 A1 | | 1/2008 |

OTHER PUBLICATIONS

UK Search Report of Application No. GB0613626.1, Dated Nov. 8, 2006, 1 page.

* cited by examiner

*Primary Examiner* — Janet Epps-Smith
(74) *Attorney, Agent, or Firm* — Egbert Law Office, PLLC

(57) ABSTRACT

A material for indelibly and uniquely marking an article for identification purposes includes a mixture including between about 1% and 10% by weight fluorescent identifier, DNA, and the remainder including predominantly a solvent.

24 Claims, No Drawings

MARKING MATERIAL

This invention relates to a material for indelibly and uniquely marking an article, and more particularly but not exclusively to a material which is dispersed as an aerosol to mark an article being an intruder in a secure area, or to mark an assailant, or to security mark articles.

Materials with unique identifiers are known for example from GB-A-2319337, for use in security marking articles so that the articles can be identified. In WO2004/086323 there is described the use of an explosive charge to disperse material including uniquely coded DNA onto an attacker, so that evidentially, an accused attacker can be proved to have been present at a crime scene.

The present invention provides a material particularly but not exclusively for use as an aerosol for spraying using a propellant gas, with a new or improved formulation.

According to a first aspect of the present invention we provide a material for indelibly and uniquely marking an article for identification purposes, the material including a mixture including between 1% and 10% by weight fluorescent identifier, DNA, and the remainder including predominantly a solvent.

By providing at least 1% of fluorescent identifier, the detection of the material under UV light is enhanced, and the material can be detected for greater times compared to known formulations when the detectability of the material can degrade significantly over even short time periods since application.

Although the material may be applied to an article for security marking, preferably the material is intended to be dispersed as an aerosol, in which case the material may additionally include a propellant and the material may be provided in a pressurised container which has one or more nozzles from which the material is dispersible as an aerosol.

It has been found that using such a formulation, the material can sprayed at high pressures of greater than 60 psi thus enabling more of the material to be sprayed greater distances than hithertofore proposed materials.

According to a second aspect of the invention we provide a material for indelibly and uniquely marking an article for identification purposes, the material including a mixture including between 0.1% and 10% by weight fluorescent identifier, DNA, solvent, and a propellant, the material being provided in a container which is pressurised and being from the container as an aerosol. The applicant has found that the invention provides a solution of key components that reside in a state, which when activated by a propellant, may be propelled in an atomised controlled and targeted form from the container.

The container may be pressurised to a pressure of greater than 60 psi.

Desirably, the container is pressurised to a pressure of about 75 psi or higher but in any event, preferably the propellant disperses the material as an aerosol as fine particles each having a diameter of about 40-70 µm and preferably about 50 µm.

The material may include up to 34% by weight propellant, but preferably includes in the order of between 25% and 26% propellant. Although any suitable, preferably liquid, propellant may be used, preferably the propellant is Dimethyl Ether.

Desirably, the material includes between 0.5% and 5% by weight fluorescent identifier, and more desirably about 1% by weight of the material An example of a suitable fluorescent identifier for the material, is Tinopal, which is detectable with a UV light having a wavelength distinct from the wavelengths of light typically used during DNA identification. Thus the inclusion of Tinopal does not interfere with the identification of the unique DNA.

In each case, preferably the DNA is biosynthesised. The DNA can be uniquely encoded for a specific use i.e. so that the DNA in each batch of the material is unique. Such DNA is available in phials of a molecular carrier and is commercially sold under the designation of Tracetag Cipher mark security DNA. Desirably the DNA includes a unique sequence which is identifiable e.g. with a Pyrosequencer, or the DNA may be uniquely coded with chemical taggants, e.g. particular isotopes, which enable the DNA uniquely to be identified.

The DNA in its molecular carrier may account for between 9% and 10% by weight of the material. The material may contain at least $10^{15}$ DNA molecules per liter, and more desirably in excess of about $3\times10^{17}$ molecules. However it will be appreciated that the number of the uniquely coded DNA molecules required for identification purposes will depend on the sensitivity of the identification equipment and/or skill of a DNA identification operative.

Because the material may be stored for long periods e.g. in a container from which the material may be sprayed, to protect the material from degradation, preferably the material includes a preservative, such as Sodium Benzoate, which may account for between 0.1% and 3% by weight of the material.

The solvent may be water.

The material may be covert material i.e. colourless so that when applied to an article, e.g. sprayed onto an intruder or attacker, the material cannot be seen other than with UV light of a wavelength suitable for seeing the fluorescent identifier. However alternatively, the material may be overt i.e. may contain a highly visible and durable stain. One suitable material for such a stain is Erythrosine which is a red/orange dye being an Iodoeosine Sodium salt, such as Tetraiodofluorescein Sodium salt.

By including both fluorescent identifier and highly visible stain, a person who has been sprayed with the material for example, may do his/her best to remove the stain, unawares that the fluorescent identifier still enables the material to be seen under suitable UV light, and the specific material identified through the unique DNA.

Where the material is overt, preferably the material includes between 0.1% and 10% by weight highly visible coloured stain, and more desirably about, 1% by weight stain.

According to a third aspect of the invention we provide a method of marking an article indelibly and uniquely for identification purposes, utilising a material according to the first or second aspect of the invention.

According to a fourth aspect of the invention we provide a pressurised container including material according to the first or second aspect of the present invention, the container being pressurised by the propellant.

Examples of the invention will now be described.

EXAMPLE 1

A covert colourless material having a volume of about 31 ml was prepared, with the following formulation, in a pressurised container, namely:—

| | |
|---|---|
| Tinopal/Sigma fluorescent identifier 28 | 0.68% by weight |
| Sodium Bezoate BP food grade preservative | 1% by weight |
| Tracetag Cipher mark security DNA having about $10^{14}$ DNA molecules in 3 ml of molecular carrier | 9.68% by weight |

-continued

| | |
|---|---|
| Dimethyl Ether propellant | 25.8% by weight |
| Water (solvent) | 62.84% by weight |

The material was provided in a 35 ml pressurised container, with a release mechanism connected to an intruder detector system in a secure area inside a building. The container was pressurised to about 75 psi.

The intruder detector system was armed so that in the event of an intruder being detected, the release mechanism of the container would be operated to release the pressure in the container through a nozzle to produce an aerosol of fine particles of the material each having a diameter of about 50 µm.

The nozzle (or nozzles) were arranged widely to disperse the material so that at least some of the material would be applied to the detected intruder.

By virtue of the fluorescent identifier, notwithstanding that the material is clear, the presence of the material is detectable by UV light of a wavelength suitable for detecting the Tinopal. Upon identifying the presence of the material, further testing to extract and identify the particularly coded DNA would, upon comparison with a database of such DNAs, evidentially establish the presence of the intruder in the secure area.

EXAMPLE 2

An overt material with the following formulation was prepared and again placed in a pressurised container as in Example 1, namely:—

| | |
|---|---|
| Tinopal/Sigma fluorescent identifier 28 | 1% by weight |
| E127 Erythrosine PWD 24107 | 1% by weight |
| Sodium Bezoate BP food grade preservative | 1% by weight |
| Tracetag Cipher mark security DNA having about $10^{14}$ DNA molecules in 3 ml of molecular carrier | 9.68% by weight |
| Dimethyl Ether propellant | 25.8% by weight |
| Water (solvent) | 61.52% by weight |

Again, the material was provided in a 35 ml pressurised container, with a release mechanism connected to an intruder detector system in a secure area inside a building. Again the contents of the container were pressurised to a pressure of about 75 psi.

The intruder detector system was armed so that in the event of an intruder being detected, the release mechanism would be operated to release the pressure in the container through a nozzle to produce an aerosol of the material in which the material has a density of between 50 and 100 dpi and preferably predominantly about 75 psi. The nozzle (or nozzles) were arranged widely to disperse the material so that at least some of the material would be applied to the detector intruder.

By virtue of the stain, an intruder marked with the material would be aware of the presence of the material. Erythrosine is extremely durable and indelible whether applied to clothing or the skin, and this would present a considerable difficulty to an intruder attempting to conceal his presence in the secure area. However, even if the intruder was able to clean off or otherwise conceal the stain, the Tinopal, which is colourless, would still indicate the presence of the material. Again, further testing to extract and identify the particularly coded DNA would, upon comparison with a database of such DNA, evidentially establish the presence of the intruder in the secure area.

Various modifications are possible to the covert and overt material. For example the proportion of Tinopal in either, could be anywhere between 0.1% and 10% by weight of the material, although it has been established through testing that providing less than 1% by weight Tinopal or other suitable fluorescent identifier, may not provide sufficient durability particularly if applied to the article other than by aerosol dispersal at high pressures of greater than 60 psi. Where the proportion of Tinopal is greater than 1%, the material more readily lends itself to application other than by aerosol dispersal, or at least by aerosol dispersal at pressures of 60 psi or less.

In each case though preferably where the material is dispersed as an aerosol, the particles have diameters of about 50 µm, or at least the average particle size is of this order.

Instead of Tinopal another suitable fluorescent identifier, which is visible under UV light which preferably is of a distinct wavelength to that of light used in any DNA identification process, may be used.

Although Dimethyl Ether is the preferred propellant, another liquid propellant may be provided to provide pressure in the container to enable the material to be dispersed from the container to the desired density and for a large distance. More or less propellant than that in the formulations above may be used, up to a recommended maximum of 34% where water is present.

Instead of a Sodium Benzoate BP preservative being used, another suitable preservative may be used where this is required.

Although in each of the examples of the invention, the material formulated is intended for dispersal as an aerosol by a propellant, in another example the material may otherwise be dispersed for application to an article such as an intruder or assailant, or may be simply be applied for security marking as required to an object.

In each case, it will be appreciated that the uniquely encoded DNA molecules will tend to attach to other chemicals of the material and/or to the article (i.e. intruder/assailant or object), and most particularly to chemicals of an organic nature, making removal of the DNA very difficult.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An article for indelibly and uniquely marking an article for identification purposes, the article comprising:
   a mixture having between about 0.1% and 10% by weight of a fluorescent identifier, a DNA, solvent and a propellant, said mixture being provided in a pressurized container which has one or more nozzles from which said mixture is dispersable as an aerosol, wherein said container is pressurized to a pressure greater than 60 p.s.i., and wherein said propellant disperses said mixture as the aerosol of fine particles each having a diameter of between 40 µm and 70 µm, said mixture having at least $10^{15}$ DNA molecules per liter.

2. The article of claim 1, said container being pressurized to a pressure of approximately 75 p.s.i.

3. The article of claim 1, each of said particles having a diameter of approximately 50 µm.

4. The article of claim 1, said mixture having between 25% and 26% by weight of said propellant.

5. The article of claim 1, said propellant being dimethyl ether.

6. The article of claim 1, said mixture having between 0.5% and 5% by weight of said fluorescent identifier.

7. The article of claim 6, said mixture having approximately 1% by weight of said fluorescent identifier.

8. The article of claim 1, said fluorescent identifier being detectable by ultraviolet light.

9. The article of claim 1, said DNA being biosynthesised.

10. The article of claim 1, said DNA being uniquely encoded.

11. The article of claim 1, said DNA having an identifiable unique sequence therein.

12. The article of claim 1, said DNA being uniquely coded with chemical taggants.

13. The article of claim 1, further comprising a molecular carrier, said DNA and said molecular carrier being between 9% and 10% by weight of said mixture.

14. The article of claim 1, said mixture having approximately $3 \times 10^{17}$ DNA molecules per liter.

15. The article of claim 1, said mixture having a preservative.

16. The article of claim 15, said preservative being sodium benzoate.

17. The article of claim 15, said preservative being between 0.1% and 3% by weight of said mixture.

18. The article of claim 1, said solvent being water.

19. The article of claim 1, said mixture containing an overt material with a visible and durable stain.

20. The article of claim 19, said stain being erythrosine.

21. The article of claim 19, said stain being between 0.1% and 10% by weight of said mixture.

22. The article of claim 21, said stain being 1% by weight of said mixture.

23. The article of claim 1, said propellant pressurizing said container.

24. An article for indelibly and uniquely marking an article for identification purposes, the article comprising:

A mixture having between 0.1% and 10% by weight of a fluorescent identifier, DNA and a remainder of the mixture being predominately a solvent, said mixture being provided in a pressurized container having a propellant therein which has one or more nozzles from which said mixture is dispersable as an aerosol wherein said pressurized container is pressurized to a pressure of greater than 60 p.s.i., wherein said aerosol has particles each having a diameter of between 40 µm and 70 µm, said mixture having at least $10^{15}$ DNA molecules per liter.

* * * * *